United States Patent
von Hirtz

(10) Patent No.: US 10,976,226 B2
(45) Date of Patent: Apr. 13, 2021

(54) STEAM SAMPLE CONCENTRATOR AND CONDITIONER FOR ON-LINE STEAM PURITY ANALYSIS

(71) Applicant: Thermochem, Inc., Santa Rosa, CA (US)

(72) Inventor: Paul von Hirtz, Santa Rosa, CA (US)

(73) Assignee: THERMOCHEM, INC., Santa Rosa, CA (US)

(*) Notice: Subject to any disclaimer, the term of this patent is extended or adjusted under 35 U.S.C. 154(b) by 320 days.

(21) Appl. No.: 16/246,961

(22) Filed: Jan. 14, 2019

(65) Prior Publication Data
US 2020/0225130 A1    Jul. 16, 2020

(51) Int. Cl.
*G01N 1/40*    (2006.01)
*G01N 11/06*    (2006.01)

(52) U.S. Cl.
CPC ........... *G01N 1/4022* (2013.01); *G01N 11/06* (2013.01); *G01N 2001/4033* (2013.01)

(58) Field of Classification Search
None
See application file for complete search history.

(56) References Cited

U.S. PATENT DOCUMENTS

| | | | | |
|---|---|---|---|---|
| 4,426,880 A | * | 1/1984 | Walters | G01N 17/008 73/61.62 |
| 4,472,355 A | * | 9/1984 | Hickam | G01N 1/40 159/1.1 |
| 4,736,590 A | * | 4/1988 | Monticelli, Jr. | G01N 21/85 60/641.2 |
| 4,978,506 A | * | 12/1990 | Calderwood | G01N 17/00 210/263 |

* cited by examiner

*Primary Examiner* — Lisa M Caputo
*Assistant Examiner* — Nigel H Plumb
(74) *Attorney, Agent, or Firm* — Casimir Jones, S.C.; Melissa Karabinis

(57) ABSTRACT

The present invention relates to a steam sample concentrator and conditioning (SSCC) system. The SSCC finds use in concentrating impurities carried in steam (e.g., used in power generation and other industrial processes) and facilitating steam analysis.

27 Claims, 8 Drawing Sheets

FIG. 7

SSCC Separator Efficiency Test

| Test Step Description | Tracer in Separator Condensate mg/kg | Tracer in Separator Steam mg/kg | Carry-over of Separator Condensate % Moisture |
|---|---|---|---|
| 8-27-18  12:00  Background | <0.02 | <0.02 | 0% |
| 8-27-18  12:37  Tracer Injection | 770 | 1.39 | 0.18% |
| 8-27-18  12:44  Tracer Injection | 860 | 1.97 | 0.23% |
| 8-27-18  12:48  Tracer Injection | 991 | 2.28 | 0.23% |
| 8-27-18  12:54  Tracer Injection | 1160 | 1.96 | 0.17% |
| 8-27-18  12:59  Tracer Injection | 933 | 1.54 | 0.17% |
| 8-27-18  13:01  Tracer Injection | 933 | 1.55 | 0.17% |

Note: Injected Tracer is PTSA, 1% solution at 10 g/minute to sample inlet steam line

FIG. 8

SSCC Steam Impurity Recovery Test

| Test Step Description | Sodium mg/kg |
|---|---|
| 10-05-18  14:01  Background | 0.01 |
| 10-05-18  14:50  NaCl Injection | 0.75 |
| 10-05-18  15:00  NaCl Injection | 0.89 |
| 10-05-18  15:04  NaCl Injection | 1.10 |
| 10-05-18  15:07  NaCl Injection | 1.10 |
| 10-05-18  15:10  NaCl Injection | 1.04 |
| 10-05-18  15:12  NaCl Injection | 1.04 |
| Average: | 0.99 |
| Recovery of Injected Impurity: | 97% |

Note: Injected NaCl solution is 10.3 ppm Na at 9.8 g/minute to sample inlet steam line, Condensate flowrate is 0.0994 g/min, expected Na concentration in sample is 1.02 mg/kg

STEAM SAMPLE CONCENTRATOR AND CONDITIONER FOR ON-LINE STEAM PURITY ANALYSIS

FIELD OF THE APPLICATION

The present application is directed to a steam sample concentrator and conditioning (SSCC) system and methods of using the same.

BACKGROUND OF THE INVENTION

Steam used in fossil fuel, nuclear and geothermal power plants contains impurities such as silica, sodium, chloride, iron and solid particles which can cause corrosion, scaling and erosion of power plant equipment, especially steam turbines. Steam used in other industrial processes such as enhanced oil recovery (e.g., steam flood injection), heating, cooling, food processing and medical sterilization applications may also contain impurities detrimental to the processes. Impurities are present as dissolved species in liquid water droplets entrained in the steam, or as solid particulate material. Volatile silica and chloride may exist in high-temperature saturated steam or in superheated geothermal steam produced from geothermal wells that tap deep high-temperature reservoirs of water and/or steam. Determining the amount of these impurities in steam is important for process control and for successfully implementing mitigation measures to improve the steam purity and prevent equipment damage.

Impurities carried in liquid droplets or as solid particles have a much higher density than the surrounding gaseous steam phase. Isokinetic sampling is required to obtain representative samples followed by specialized analytical techniques for low-level detection in the presence of various interfering species in the steam condensate sample. Geothermal steam contains $H_2S$ and $CO_2$ which cause severe interferences in most analytical methods required for laboratory and on-line analysis of steam impurities. Typically, measurement down to 10 ppb or less in steam for sodium, silica, chloride and iron is required to prevent scaling, erosion and corrosion in steam turbines and other process equipment. Detection at these levels can be very difficult, especially in the presence of interfering species. Commercial Analyzers may be able to reach these detection limits in ultra-pure steam condensate free of dissolved gases, but not reliably in process steam and never in raw geothermal steam.

On-line measurement of steam purity is a well-established technique that is considered critical to power generation and other industrial processes utilizing steam. Conventional techniques involve 100% condensation of the steam sample, typically collected isokinetically. The steam is fully condensed, and the resulting liquid condensate is sub-cooled (below the water vapor saturation temperature at the condensing pressure) in a continuous single-step process through a helical tube heat exchanger with the steam flowing through the inside of the tubing (tube side) and cooling water on the outside of the tubing (shell side). The concentration of impurities by mass measured in this fully-condensed steam condensate is the same as in the bulk steam flow in the pipeline or process from which it was extracted. There are no corrections required for dilution or concentration of the condensate sample impurity concentrations by mass back to the original steam.

In the process of fully condensing the steam sample and sub-cooling the condensate, a two-phase mixture of liquid steam condensate and noncondensable gas is produced. The noncondensable gases dissolve into the condensate through the condensing apparatus in proportion to their partial pressure and solubility constant at the condensate outlet temperature, which is typically 20 to 30 C (well below the boiling temperature at 1 atm). Under these conditions, $H_2S$ and $CO_2$ are highly soluble. Efforts have been made in geothermal applications to remove these gases from the condensate after they have dissolved in the conventional condensing processes described above, by purging the sub-cooled condensate with nitrogen, reheating the condensate (below boiling) and/or passing the condensate through a degassing membrane where dissolved gases permeate through the membrane to a flowing gas stream of higher purity gas such as nitrogen. Of critical importance to the success or failure of impurity measurement in geothermal steam, particularly silica measurement, is the effective removal of $H_2S$ when there is $NH_3$ present in the steam. Conventional techniques are insufficient to fully remove $H_2S$ and prevent analytical interferences in the presence of $NH_3$. This is because the dissolution of highly soluble $NH_3$ gas raises the pH of the condensate, resulting in ionization of $H_2S$ to bisulfide ions:

$$NH_3 + H_2O \rightarrow NH_4^+ + OH^-$$

$$OH^- + H_2S \rightarrow H^+ HS^-$$

The bisulfide ions cannot be purged or degassed out of the condensate because they are ions and have no vapor pressure. The only means possible to completely purge $H_2S$ from condensate after the conventional condensation process is to lower the pH to 3.0 or less through the addition of acid, converting all bisulfide back to $H_2S$:

$$H^+ HS^- \rightarrow H_2S.$$

SUMMARY OF INVENTION

The present invention provides a steam sample concentrator and conditioning (SSCC) system (e.g., to pretreat steam prior to analyses and/or use). The SSCC can be used to concentrate impurities carried in steam (e.g., used in power generation and other industrial processes) and to facilitate analysis (e.g., at a part per billion (ppb) level) of steam impurities such as sodium (Na), silica (SiO2), chloride (Cl), iron (Fe) and total suspended solids (TSS). The SSCC can also be used to prevent the dissolution of non-condensable gases (NCG) from the steam (e.g., geothermal steam) into the condensate that interfere with steam analyses thereby allowing accurate measurement of the impurities in a steam sample.

Accordingly, in some embodiments, the invention provides a steam sample concentrator and conditioning (SSCC) system, and methods of using the same, as disclosed and described herein. In some embodiments, the SSCC system concentrates impurities carried in steam. The invention is not limited by the type of impurity concentrated. Exemplary impurities that are concentrated include, but are not limited to, sodium (Na), silica (SiO2), chloride (Cl), iron (Fe), total suspended solids (TSS), or other impurities known in the art. In some embodiments, the impurity or impurities are those that cause corrosion, scaling and/or erosion of equipment (e.g., power plant equipment (e.g., a steam turbine)). In some embodiments, the impurity is present as a dissolved species (e.g., in liquid water droplets in the steam). In other embodiments, the impurity is present as a solid particulate material. The invention is not limited by the type of steam treated (e.g., pretreated) using a SSCC system of the invention. In some embodiments, the steam is steam used for power generation (e.g., geothermal steam). Examples of other types of steam treated include, but are not limited to, steam used for oil recovery (e.g., steam flood injection), steam used for heating, steam used for cooling, steam used for food processing, and steam used for medical sterilization applications.

In some embodiments, the SSCC system facilitates analysis of one or more impurities present in steam (e.g., that impede analysis of a steam sample). The invention is not limited by the type or source of the one or more impurities analyzed. Exemplary impurities analyzed include, but are not limited to, sodium (Na), silica (SiO2), chloride (Cl), iron (Fe), total suspended solids (TSS), or other impurity known in the art. In some embodiments, the analysis determines the amount or level of one or more impurities in steam. The invention is not limited by the level of the impurities measured, detected, and/or determined. In some embodiments, analysis (e.g., measurement and/or detection) of the impurities occurs at a part per billion (ppb) level. However, the invention is not so limited. The range of impurities measured, detected, and/or determined in steam can be from about 0.1 ppb to over about 10,000 ppb, although smaller (e.g., less than 0.1 ppb) and larger (e.g., greater than 10,000 ppb) amounts of impurities may be measured, detected, and/or determined. In some embodiments, the SSCC system concentrates impurities carried in steam and facilitates the analysis (e.g., measurement and/or detection) of the impurities. In some embodiments, determining the amount of one or more impurities in steam provides superior process control. In other embodiments, determining the amount of one or more impurities in steam makes implementing mitigation measures possible (e.g., to improve steam purity and/or prevent equipment damage) that are not possible in the absence of accurately determining the amount of the one or more impurities.

In some embodiments, the SSCC system is used to prevent the dissolution of noncondensable gases (NCGs) in geothermal steam. In some embodiments, prevention of dissolution of NCGs in steam allows a more accurate measurement of NCGs in a steam sample (e.g., a sample after separation of condensate and noncondensable gas phases) compared to measurements taken in the absence of preventing dissolution of NCGs in steam. The invention is not limited by the type of NCGs (e.g., the dissolution into steam of which is prevented). In some embodiments, the NCG is hydrogen sulfide ($H_2S$). In some embodiments, the NCG is carbon dioxide ($CO_2$). In some embodiments, the NCG is a mixture of gases (e.g., $H_2S$ and $CO_2$, $H_2S$ and $CO_2$ and one or more other gases).

The invention also provides a method of analyzing a sample (e.g., a steam sample or portion thereof (e.g., a steam stream sample)) using a SSCC system of the invention. In some embodiments, a steam sample is collected (e.g., using a fixed multi-nozzle isokinetic sample probe). In some embodiments, the sample (e.g., sample stream) is directed under pressure to the SSCC system through tubing (e.g. stainless-steel tubing). In some embodiments, the sample point and the SSCC system are separated by about 1-50 meters (m), about 5-25 m, about 5-15 m, about 7-15 m, or about 7-10 m. In some embodiments, the SSCC is within about 10 m from the sample point. In some embodiments, the steam sample flow is regulated to maintain isokinetic flow conditions (e.g., using a critical flow device). The invention is not limited by the type of flow device used. Exemplary flow devices include, but are not limited to, a differential pressure orifice meter, a critical flow orifice, a vortex flowmeter, a coriolis flowmeter and a thermal mass flow meter. In still other embodiments, a desuperheat pump recirculates condensate to ensure the sample remains saturated and does not deposit any impurities upstream of the Analyzers. In some embodiments, a metering pump doses acid into the sample stream after the desuperheater. The invention is not limited by the type of acid introduced into the sample stream via the metering pump. Exemplary acids include, but are not limited to, HCl, $H_2SO_4$, acetic acid, and citric acid. In some embodiments, the acid is a dilute acid (e.g., a concentrated acid that has been diluted by adding it to water). In some embodiments, the steam sample is condensed (e.g., partially condensed) under a controlled (e.g., precisely controlled) condensation process in a single-tube shell-and-tube heat exchanger. In further embodiments, the fraction of condensate produced is adjusted (e.g., automatically by varying the flowrate of cooling water through the single-tube heat exchanger) to a desired set-point. The invention is not limited by the fraction of condensate produced. In some embodiments, the fraction is between about 2-50% of the total sample steam flow. In other embodiments, the fraction is between about 5-10% of the total sample steam flow. Since impurities (e.g., sodium (Na), silica (SiO2), chloride (Cl), iron (Fe), total suspended solids (TSS), and/or other impurities of interest) are highly soluble at the condensation temperature (e.g., 100 to 150 C), the impurities are concentrated in the process (e.g., by a factor of 2 to 50 times). In some embodiments, the high-temperature partial condensation process with acid addition to maintain the pH below 3.0 prevents noncondensable gases from dissolving (e.g., eliminating steps and/or resources (e.g., $H_2S$) needed to degas the condensate at a later time). In some embodiments, the separated NCG is measured by a mass flow meter to determine the NCG concentration in the steam. In a further embodiment, the concentrated and degassed liquid sample is pumped to an on-line Analyzer (e.g., for measurement of sodium, silica, chloride, iron and/or turbidity levels).

The SSCC system and methods of using same provided in some embodiments of the invention possess unique and fundamental advantages for on-line monitoring for steam purity (e.g., for geothermal steam purity). In some embodiments, a system and method of using the same described herein permits sample preconcentration by an order of magnitude or more (e.g., 10-20 times) above raw levels in steam. In further embodiments, a system and method of using the same described herein comprises a sample condensation process that prevents dissolution of interfering species (e.g., <0.1% of $H_2S$ and $CO_2$ in steam are dissolved in the condensate sample). In still further embodiments, condensation without gas dissolution makes possible highly accurate NCG measurements not possible without a system and method disclosed herein. In still other embodiments, a system and method of using the same described herein comprises isokinetic sample flowrate control (e.g., by controlling the flow of the sample steam through the use of a critical flow orifice or automatic flow control valve, thereby ensuring the isokinetic probe is operated at the correct flowrate to produce a representative sample of steam vapor and liquid and/or particulate impurities). In yet other embodiments, a system and method of using the same described herein eliminates the need for air and/or nitrogen purging (e.g., required for interference removal). A system and method of using the same described herein also eliminates, in some embodiments, the need for ion-exchange cartridges (e.g., otherwise required for preconcentration or pre-treatment).

BRIEF DESCRIPTION OF DRAWINGS

FIG. 7 shows the results of a test performed on the SSCC using a steam test loop to determine the amount of liquid carry-over into the steam from the separator 9 showing that the amount of liquid carry-over with the steam from the separator was only about 0.2%.

FIG. 8 shows the results of a test performed to directly measure the concentration factor and recovery efficiency of steam impurities through the SSCC process and shows that under the conditions tested the expected concentration of Na in the condensate was 1.02 ppm and the average measured concentration by the on-line sodium Analyzer was 0.99 ppm.

DETAILED DESCRIPTION

Figure 1:
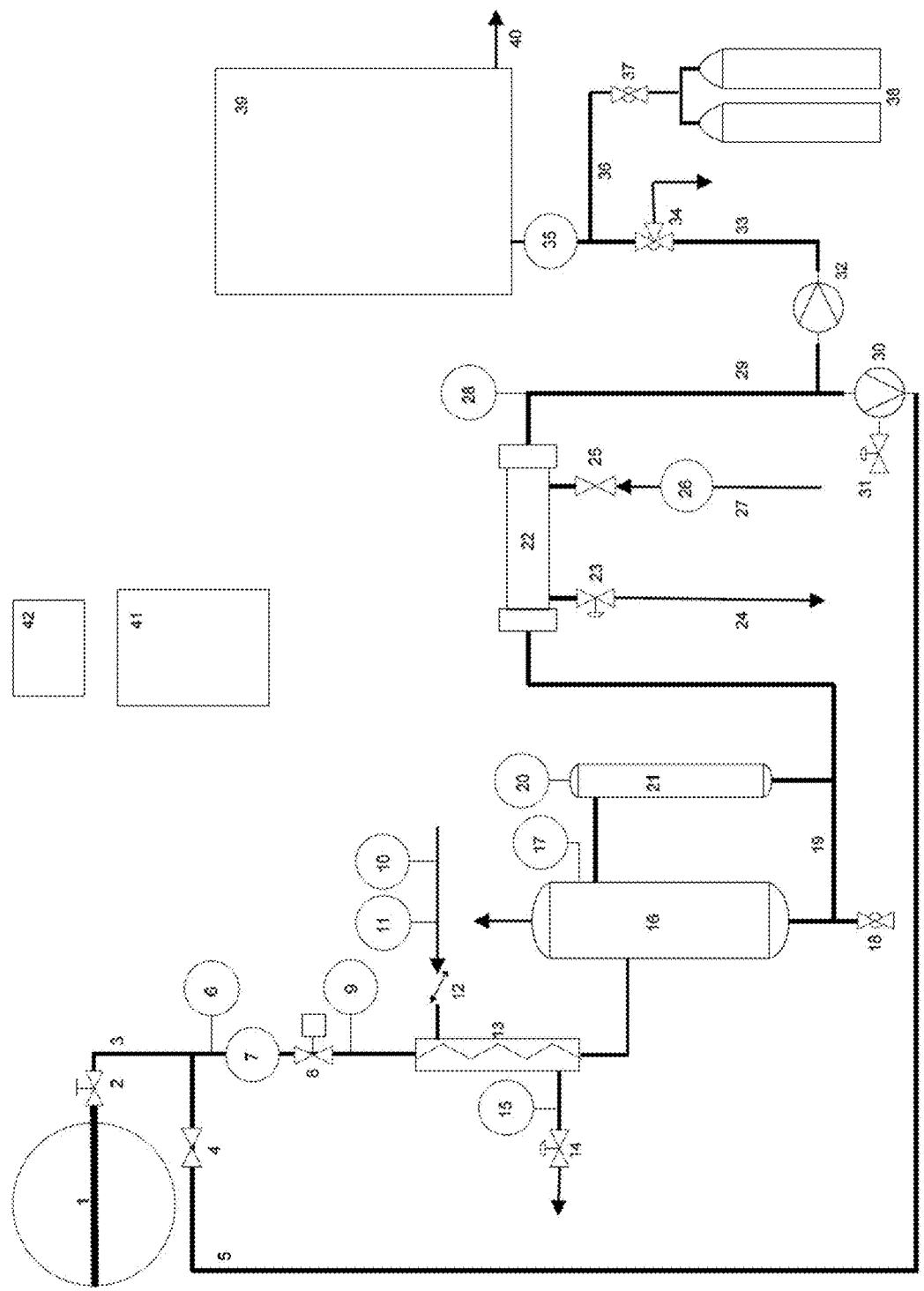
FIG. 1 is a diagram depicting the major components and sub-components and overall structure of a SSCC system in one embodiment of the invention connected to an on-line stream purity Analyzer.

The present invention relates to a steam sample concentrator and conditioning (SSCC) system. The SSCC system concentrates impurities carried in steam and facilitates analysis of the impurities. The SSCC system prevents the dissolution of noncondensable gases (NCGs) (e.g., hydrogen sulfide ($H_2S$) and carbon dioxide ($CO_2$)) in geothermal steam that interfere with steam analysis. For example, when steam is analyzed, it is often separated into condensate and noncondensable gas phases. The SSCC system of the invention, via prevention of the dissolution of NCGs in a steam sample after separation of condensate and noncondensable gas phases, enables a significantly more accurate measurement of the impurities in the sample compared to conventional systems.

The SSCC system of the invention can be configured to interface with commercial on-line analysis instruments for the analysis of the impurities. Non-limiting examples of commercial analysis instruments are Hach (Hach, Loveland, Colo., USA) Model 9245 low-level sodium Analyzer based on ion-specific electrode (ISE); Hach Model 5500sc low-level silica Analyzer based on color spectrophotometry; Hach Model EZ2005 low-level total iron Analyzer based on color spectrophotometry; and/or Hach Model TU5300 low-level turbidity (TSS) Analyzer based on laser light scattering.

The concentrated and interference-free liquid sample generated by the SSCC system that is provided to the Analyzer greatly improves the reliability of on-line steam purity measurement by reducing the chance of false positive results for impurities and bias towards erroneous elevated values, which is common when performing measurements on samples that have not been treated due to contamination by these same compounds ubiquitously found in the environment and the aforementioned interferences from dissolved gases. Thus, the SSCC system disclosed herein, by 1. increasing the sample concentration an order of magnitude directly in the sample collection process; and 2. preventing the dissolution of NCGs, reduces and/or eliminates false positive readings (e.g., caused by impurities and bias towards erroneous elevated levels) and reduces and/or eliminates interference from dissolved gases (e.g., $H_2S$ and/or $CO_2$) associated with conventional steam sample analysis systems.

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention.

A non-limiting example of a SSCC system of the invention is shown in FIG. 1. The same example is shown in FIG. 2 with the electrical signal and control interconnections with the Programable logic control (PLC) system.

Figure 2:
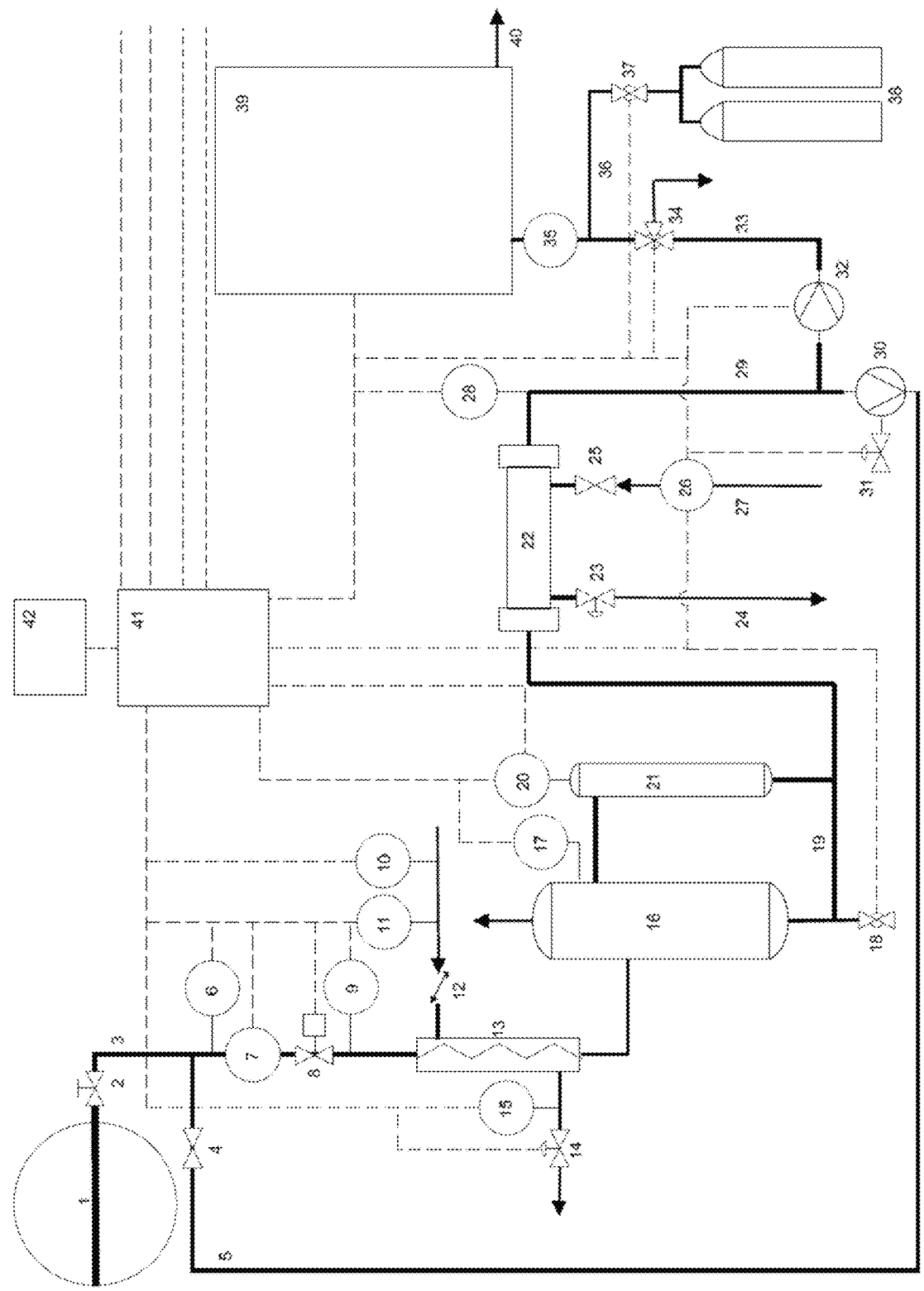
FIG. 2 is a diagram depicting the major components and sub-components with electrical analog and digital signal connections (dashed lines, control inputs and signal outputs) between the components of a SSCC system in one embodiment of the invention.

Listed below by number, as shown in FIGS. 1 and 2, are major components and subcomponents of a SSCC system, in one embodiment of the invention, with a brief description of the function and interrelationship of each in a SSCC of the invention:

1. Isokinetic Probe.
   a. In some embodiments, a SSCC comprises a isokinetic probe (e.g., used to extract a representative sample (mixture) of liquid- and solid-phase impurities in steam from a pipeline through which the power plant/process steam flows).

2. Isolation Valve for Isokinetic Probe.
   a. In some embodiments, a SSCC comprises an isolation valve (e.g., utilized to shut-off of the steam sample flow from the isokinetic probe to SSCC).

3. Steam Sample Line to SSCC.
   a. In some embodiments, a SSCC comprises a steam sample line (e.g., a piping conduit for steam sample flow from the probe to SSCC).

4. Isolation Valve for Desuperheat Condensate Injection into Steam Sample Line.
   a. In some embodiments, a SSCC comprises an isolation valve for desuperheat condensate injection into steam sample line (e.g., that allows shut-off of recirculated condensate back into the steam sample flow to the SSCC (e.g., for purposes of desuperheating the steam sample)).

5. Piping for Desuperheat Condensate from Desuperheat Pump.
   a. In some embodiments, a SSCC comprises piping that provides a conduit for the recirculated condensate from the sample cooler back into the steam sample flow steam.
6. Pressure Sensor in Steam Sample Line.
   a. In some embodiments, a SSCC comprises a pressure sensor (e.g., that measures pressure upstream of the steam sample flowmeter and/or transmits signals to a Programable logic controller (PLC) component of the SSCC (e.g., for flowrate computation)).
7. Flowmeter for Steam Sample.
   a. In some embodiments, a SSCC comprises a flowmeter (e.g., that measures steam sample flowrate and/or transmits signals to a PLC of the SSCC (e.g., in order to calculate and/or adjust the % of isokinetic flowrate and the steam sample concentration factor)).
8. Flow Control Valve/Shut-Off Valve for Steam Sample.
   a. In some embodiments, a SSCC comprises a flow control valve/shut off valve (e.g., for the steam sample line (e.g., that controls the steam sample flowrate based on an input signal from PLC (e.g., in order to maintain the isokinetic flowrate close to 100%) and/or automatically shuts-off the steam sample flow when the system or process triggers an alarm condition).
9. Temperature Sensor for Steam Sample.
   a. In some embodiments, a SSCC comprises a temperature sensor (e.g., that measures the temperature downstream of the steam sample flowmeter and transmits the signal to PLC for steam saturation/superheat calculation).
10. Pressure Switch for Contactor Cooling Water Supply.
    a. In some embodiments, a SSCC comprises a pressure switch (e.g., that measures the cooling water pressure to the contactor and/or transmits an alarm to the PLC when the pressure is below a pre-set value).
11. Temperature Sensor for Contactor Cooling Water Supply.
    a. In some embodiments, a SSCC comprises a temperature sensor for contactor cooling water supply (e.g., that measures the cooling water temperature to the contactor and/or transmits the value to the PLC, triggering an alarm when above a pre-set value).
12. Check Valve for Contactor Cooling Water Supply.
    a. In some embodiments, a SSCC comprises a check valve (e.g., for contactor cooling water supply (e.g., that prevents back-flow of cooling water from contactor)).
13. Steam Contactor.
    a. In some embodiments, a SSCC comprises a steam Contactor (e.g. that provides controlled heat-transfer from the steam sample to the cooling water (e.g., providing a constant amount of condensed steam, concentrated in non-volatile impurities that are scrubbed (contacted) from the steam sample)).
14. Flow Control Valve for Contactor Cooling Water Outlet.
    a. In some embodiments, a SSCC comprises a flow control valve for contactor cooling water outlet (e.g., that controls (e.g., via programmed logic) the cooling water flowrate out of the contactor (e.g., based on an input signal from PLC in order to maintain a target condensate flowrate)).
15. Temperature Sensor for Contactor Cooling Water Outlet.
    a. In some embodiments, a SSCC comprises a temperature sensor for contactor cooling water outlet (e.g., that measures the cooling water temperature from the contactor outlet and/or transmits the value to the PLC, triggering an alarm when above a pre-set value).
16. Steam/Condensate Separator.
    a. In some embodiments, a SSCC comprises a steam/condensate separator (e.g., that separates the condensate from the residual steam exiting the contactor (e.g., by centrifugal action, inertial separation and wire mesh media entrapment)).
17. Separator Pressure Sensor.
    a. In some embodiments, a SSCC comprises a pressure sensor at the separator (e.g., that measures the pressure at the separator outlet and/or transmits the value to the PLC, triggering an alarm when above a pre-set value).
18. Separator Condensate Dump Valve.
    a. In some embodiments, a SSCC comprises a condensate dump valve at the separator (e.g., that allows excess condensate to drain (e.g., via programmed logic) from the separator (e.g., based on an input signal from PLC when a high-level alarm is triggered in accumulator)).
19. Separator Condensate Piping to Sample Cooler.
    a. In some embodiments, a SSCC comprises piping for transfer of separator condensate to sample cooler (e.g., a piping conduit for the condensate from the separator to the sample cooler, inter-tied to an accumulator).
20. Accumulator Level Sensor.
    a. In some embodiments, a SSCC comprises level sensor of an accumulator component of the SSCC (e.g., that measures the level in the accumulator and/or transmits a signal to the PLC (e.g., in order to allow control of the VSD condensate pump and/or maintain a constant liquid level in the accumulator and separator)).
21. Accumulator Vessel.
    a. In some embodiments, a SSCC comprises an accumulator vessel (e.g., that provides a vessel free of flow turbulence that reflects the same liquid level as in the separator.
22. Condensate Sample Cooler.
    a. In some embodiments, a SSCC comprises a condensate sample cooler (e.g., a single-tube heat exchanger or equivalent (e.g., that cools the condensate sample from the condensation temperature (e.g., from about 100-115 C to less than 50 C))).
23. Flow Control Valve for Condensate Sample Cooler Cooling Water Outlet.
    a. In some embodiments, a SSCC comprises a flow control valve at the condensate sample cooler cooling water outlet (e.g., that provides manual flow control for the cooling water to the sample cooler).
24. Condensate Sample Cooler Cooling Water Outlet Piping.
    a. In some embodiments, a SSCC comprises piping for the condensate sample cooler cooling water outlet (e.g., that provides a conduit for the cooling water from the sample cooler to drain).
25. Condensate Sample Cooler Cooling Water Inlet Isolation Valve.
    a. In some embodiments, a SSCC comprises a condensate sample cooler cooling water inlet isolation valve (e.g., that allows for manual shut-off of the cooling water flow to the sample cooler).
26. Condensate Sample Cooler Cooling Water Inlet Flow Switch.
    a. In some embodiments, a SSCC comprises a condensate sample cooler cooling water inlet flow switch (e.g., that measures the flow cooling water flow to the sample cooler and/or transmits an alarm to the PLC when the flow is below a pre-set value).

27. Condensate Sample Cooler Cooling Water Inlet Piping.
   a. In some embodiments, a SSCC comprises piping for the condensate sample cooler cooling water inlet (e.g., that provides a conduit for cooling water flow to the sample cooler).

28. Condensate Sample Temperature Sensor.
   a. In some embodiments, a SSCC comprises a condensate sample temperature sensor (e.g., that measures the temperature of the condensate sample downstream of the sample cooler and/or transmits the value to the PLC, triggering an alarm when above a pre-set value).

29. Condensate Sample Piping Outlet from Cooler.
   a. In some embodiments, a SSCC comprises piping from the condensate sample cooler (e.g., that provides a conduit for cooling water flow out of the sample cooler).

30. Desuperheat Pump.
   a. In some embodiments, a SSCC comprises a desuperheat pump (e.g., that pumps a portion of condensate from the sample cooler back into the steam sample flow to the SSCC (e.g., for desuperheating the steam sample).

31. Flow Control Valve/Shut-Off Valve for Air Supply to Desuperheat Pump.
   a. In some embodiments, a SSCC comprises a flow control valve/shut-off valve for air supply at the desuperheat pump (e.g., that allows control of compressed air supply to drive the desuperheat pump).

32. Variable-Speed Drive Condensate Sample Pump.
   a. In some embodiments, a SSCC comprises a Condensate sample pump (e.g., a variable-speed drive pump (e.g., that pumps condensate out of the accumulator vessel (through sampler cooler) with a speed in proportion to a signal from the PLC (e.g., in order to control and maintain a constant liquid level in the accumulator and separator)).

33. Condensate Sample Piping to Analyzer(s).
   a. In some embodiments, a SSCC comprises piping for Condensate sample to Analyzer(s) (e.g., that provides a conduit for cooled, pumped condensate to the Analyzer(s)).

34. Condensate Sample 3-Way Valve to Analyzer(s) or Drain.
   a. In some embodiments, a SSCC comprises a valve (e.g., a 3-way valve) for Condensate sample to Analyzer or drain (e.g., that allows the cooled, pumped condensate sample stream to drain during start-up (e.g., via programmed logic of the PLC) and/or while deionized water flows to the Analyzer(s)).

35. Condensate Sample Flow Sensor to Analyzer(s).
   a. In some embodiments, a SSCC comprises a flow sensor at the Analyzer (e.g., that measures the condensate sample flowrate and/or transmits the signal to PLC in order to calculate the steam sample concentration factor).

36. Deionized Water Piping to Analyzer(s).
   a. In some embodiments, a SSCC comprises piping for deionized water to Analyzer (e.g., that provides a conduit for deionized water to the Analyzer(s)).

37. Deionized Water Isolation Valve.
   a. In some embodiments, a SSCC comprises a isolation valve for the deionized water (e.g., that allows deionized water to flow (e.g., under control of programmed logic of the PLC) to the Analyzer(s)).

38. Deionized Water Ion-Exchange Cartridges.
   a. In some embodiments, a SSCC comprises ion exchange cartridges (e.g., that remove dissolved ions and other impurities from the deionized water supply (e.g., to produce a high-purity deionized water source to flush and provide a zero-baseline water stream to the Analyzer(s))).

39. Steam Impurity Analyzer(s).
   a. In some embodiments, a SSCC comprises one or more steam-impurity Analyzers (e.g., commercial on-line steam purity Analyzers (e.g., Na, Cl, SiO2, Fe and TSS Analyzers) that measure levels of impurities).

40. Steam Impurity Analyzer(s) Sample Drain Piping.
   a. In some embodiments, a SSCC comprises drain piping from the steam-purity Analyzer (e.g., providing a conduit for liquid to drain from the Analyzer(s)).

41. Programable Logic Control (PLC) System.
   a. In some embodiments, a SSCC comprises one or more PLC systems (e.g., providing computer-based control of the SSCC to receive input signals (e.g., from measurement instruments) and to send out control signals (e.g., to valves, pumps, the Analyzer(s) and/or the power plant control room).

42. Human—Machine Interface (HMI).
   a. In some embodiments, a SSCC comprises an HMI (e.g., a means for programming and controlling the PLC and SSCC components connected thereto (e.g., touch-screen display or equivalent).

Described below is a non-limiting example of various components of a SSCC system (e.g., as shown in FIGS. 1 and 2) of the invention and how the components function collectively to concentrate impurities carried in steam and to facilitate analysis of the impurities.

Steam Sample Extraction. A steam sample is extracted from a steam pipeline (e.g. a geothermal steam pipeline carrying raw geothermal steam) via use of a multi-nozzle isokinetic sample probe 1. In some embodiments, a multi-nozzle probe is used that provides an integrated sample of liquid- and solid-phase impurities entrained in the water vapor across the diameter of the pipeline. The Thermochem (Santa Rosa, Calif., USA) model SQ2000 multi-nozzle isokinetic steam sampling probe is designed specifically for this purpose. Other single-nozzle isokinetic steam sampling probes can be used, such as those specified under ASTM D 1066-06 "Standard Practice for Sampling Steam." In some embodiments, the multi-nozzle isokinetic sample probe is sized so that the sample flow rate at isokinetic conditions (i.e., velocity of steam into nozzle is the same as the surrounding steam velocity in pipeline) is at least 1000 g/min. However, the invention is not so limited. For example, in some embodiments, the systems and methods of the invention are useful under conditions in which the sample flow rate at isokinetic conditions is from about 100 g/min to about 10,000 g/min. In some embodiments, the minimum concentrated liquid condensate outlet sample flowrate of the steam purity Analyzer is about 10 g/min. The useable range of concentrated liquid condensate flow is from 10 g/min to 1,000 g/min. Accordingly, in one embodiment, when the total inlet steam sample flow rate is 1000 g/min, and the concentrated liquid condensate sample flowrate to the steam purity Analyzer is 50 g/min, the SSCC system provides a concentrated sample with a concentration factor of 20 (i.e., that is 20 times more concentrated than the raw inlet steam flow). The invention is not limited to any particular concentration factor. Indeed, in some embodiments, the inlet steam sample flow rate and the flowrate of the steam purity Analyzer are varied in order to provide a desired concentration factor, wherein the concentration factor is a value between about 3 and about 50, between about 5-30, between about 10 and 20, any value between 3 and 50, or any value lower than 3 (e.g., 1.5, 2, 2.5) or higher than 50 (e.g., 60, 75, 90, etc.). In a preferred embodiment, the concentration factor is a value of 10 to 20. In some embodiments, a high steam sample flowrate is utilized (e.g. 2000-10,000 g/min) by using larger isokinetic nozzle diameters (e.g., 5 mm-25 mm) thereby reducing the incidence of plugging of the nozzles by solids carried in the steam.

In some embodiments, the SSCC system comprises a component that measures the steam inlet sample flowrate. In some embodiments, the steam inlet sample flowrate is measured by a critical orifice meter, vortex meter and/or thermal mass flow meter 7. In some embodiments, when a critical orifice meter is used, the critical orifice meter provides steam sample flow regulation (e.g., required to maintain isokinetic conditions). The steam sample flowrate is linearly proportional to the upstream orifice pressure which is essentially the same as the steam pipeline pressure but can be measured directly by a pressure transducer 6 in the steam sample line 3. In embodiments when a vortex flowmeter and/or a thermal mass flowmeter are used in a SSCC system, the system also comprises a flow control valve 8.

In some embodiments, the SSCC system partially condenses the steam sample stream. The invention is not limited by the amount of partial condensation. Indeed, the SSCC system may condense the steam sample stream by about 2-50%, about 5-40%, about 5-30%, about 5-25%, or by about 5-20%, or any value therebetween. In a preferred embodiment, the SSCC system condenses the steam sample stream by about 5-20% by weight to produce a concentrated condensate sample stream (e.g., enriched in impurities). The invention is not limited by the amount of enrichment. The level of enrichment of impurities can be controlled and altered via controlling the amount of condensation of the sample stream. For example, when the sample stream is condensed by an SSCC system of the invention by about 5-20% by weight, this produces a concentrated condensate sample stream enriched in impurities by an order of magnitude.

The steam sample concentration factor=X, where X=steam inlet sample flow/condensate outlet sample flow. In some embodiments, the partial condensation process is controlled by adjusting the cooling water flowrate in a single-tube shell-and-tube heat exchanger, referred to as the Contactor 13. In such an embodiment, the cooling water supply pressure must exceed the saturation pressure of the steam sample in order to prevent boiling of the cooling water on the shell side of the heat exchanger. Typically, the steam pressure in the Contactor is 1.5 to 2.0 bara. The flowrate of the cooling water through the Contactor is regulated at the outlet by an automatic flow control valve 14 (e.g., actuated by an electronic stepper motor or by pneumatic control). Such a configuration ensures that the pressure of cooling water within the Contactor is the same as the cooling water inlet pressure and exceeds the steam sample saturation pressure, thereby preventing boiling of cooling water in the Contactor. In this way, boiling of the cooling water is avoided (e.g., that may lead to erratic slug flow and poor condensation process control). In some embodiments, the Contactor incorporates a static mixer with mixing vanes to ensure vapor/liquid contact and scrubbing of the impurities from the steam into the condensate phase 13. Thus, in some embodiments, a SSCC system of the invention (e.g., comprising one or more of an Isokinetic probe, Isolation valve for isokinetic probe, Steam sample line to SSCC, Isolation valve for desuperheat condensate injection into steam sample line, Piping for desuperheat condensate from desuperheat pump, Pressure sensor in steam sample line, Flowmeter for steam sample, Temperature sensor for steam sample, Flow control valve/shut-off valve for steam sample, Pressure switch for contactor cooling water supply, Temperature sensor for contactor cooling water supply, Check valve for contactor cooling water supply, Steam Contactor, Flow control valve for contactor cooling water outlet, Temperature sensor for contactor cooling water outlet, Steam/Condensate separator, Separator pressure sensor, Separator Condensate dump valve, Separator Condensate piping to sample cooler, Accumulator level sensor, Accumulator vessel, Condensate sample cooler, Flow control valve for Condensate sample cooler cooling water outlet, Condensate sample cooler cooling water outlet piping, Condensate sample cooler cooling water inlet isolation valve, Condensate sample cooler cooling water inlet flow switch, Condensate sample cooler cooling water inlet piping, Condensate sample temperature sensor, Condensate sample piping outlet from cooler, Desuperheat pump, Flow control valve/shut-off valve for air supply to desuperheat pump, Variable-speed drive Condensate sample pump, Condensate sample piping to Analyzer(s), Condensate sample 3-way valve to Analyzer(s) or drain, Condensate sample flow sensor to Analyzer(s), Deionized water piping to Analyzer(s), Deionized water isolation valve, Deionized water ion-exchange cartridges, Steam impurity Analyzer(s), Steam impurity Analyzer(s) sample drain piping, Programable logic control (PLC) system, and a Human—machine interface (HMI)) is configured to partially condense the steam sample stream to concentrate (e.g., by an order of magnitude) the stream and to remove bulk NCGs. A SSCC system of the invention thus functions to remove/scrub impurities from the steam stream and into the condensate phase. Thus, a SSCC system of the invention lowers the limit of detection for steam purity analysis and removes interferences (e.g., impurities) from analysis processes. For example, the detection limit typically achieved in geothermal steam using the SSCC and commercial Analyzers vs. commercial Analyzers alone are as listed below.

| Impurity | with SSSC | without SSCC |
|---|---|---|
| Sodium | 1 ppb | 20 ppb |
| Chloride | 1 ppb | 50 ppb |
| Silica | 1 ppb | 100 ppb |
| Iron | 1 ppb | 100 ppb |

In some embodiments, the SSCC system comprises a high-efficiency vapor/liquid Separator 16. A high-efficiency vapor/liquid Separator of a SSCC system of the invention, in some embodiments, is used to separate the residual steam and the condensate sample so only the concentrated and conditioned (gas-free) condensate stream is analyzed. In some embodiments, the Separator is equipped with a tangential inlet to produce cyclonic flow and a mist pad at the vapor outlet to trap residual moisture that separates the remaining steam from the condensate. The vapor/liquid Separator is highly efficient (e.g., only very small percentage (e.g., less than 5%, less than 4%, less than 3%, less than 2%, less than 1% or less) of the inlet condensate is carried-over into the residual exhaust steam. In some embodiments, the vapor/liquid Separator has a separation efficiency of >95%, >96%, >97%, >98%, or >99%. In some embodiments, the vapor/liquid Separator has a separation efficiency of >99%

(e.g., such that less than 1% of the inlet condensate is carried-over into the residual exhaust steam). In some embodiments, the SSCC system continually monitors/measures the condensate level in the Separator. Multiple ways of monitoring/measuring condensate levels may be used including, but not limited to, using magnetic level sensors and/or a pressure level sensor 20. The SSCC system may also comprise one or more components to maintain the condensate level at a constant value in the Accumulator vessel 21 including, but not limited to, a variable speed drive (VSD) condensate metering pump 32. In some embodiments, the SSCC system cools the condensate sample from about 100 C to about 30 C in a single-tube shell-and-tube heat exchanger (sample cooler) 22.

In some embodiments, a SSCC system of the invention is configured to measure both the steam sample stream flow and the condensate sample stream flow to calculate the concentration factor. In some embodiments, the concentration factor is used to correct the analyzed concentration back to the original concentration of impurity in the raw steam. In some embodiments, the SSCC system is configured such that a portion (e.g., up to 50%) of the cooled condensate is drawn from the condensate line before the VSD (Variable-speed Drive) condensate pump 32 by a high-pressure desuperheat (DSH) pump 30. The DSH pump is an air-actuated or electronic solenoid metering pump, which recirculates condensate to upstream of the critical orifice meter 7 or flow control valve 9. The recirculated condensate prevents the steam sample from becoming superheated after the critical orifice or flow control valve, which would occur upon pressure drop through the steam-flow regulating device. In some embodiments, the amount of condensate needed to maintain the steam in a saturated state with a small amount of residual moisture (~0.5%) after the pressure drop is about 50% of the condensate produced by the Contactor. In some embodiments, the SSCC system comprises a temperature sensor 9, typically an electrical resistance temperature device (RTD), that measures the temperature of the steam after the steam-flow regulating device (e.g., in order to confirm that sufficient condensate is injected by the DSH pump to produce saturated steam conditions). For example, if the steam were allowed to become superheated after the steam-flow regulating device, impurities may deposit within the sample line and reduce the apparent impurity concentrations measured downstream by the Analyzer(s) 39. Since the DSH pump condensate is recirculated in a closed loop, there is no net effect on the Accumulator level sensor 20 or the condensate flowrate from the VSD condensate pump 32.

In some embodiments, the SSCC system is configured such that the condensate stream from the VSD pump passes through an electronic 3-way solenoid valve 34 that directs the condensate to drain or to the Analyzer(s) 39. In some embodiments, the condensate sample stream flow rate is measured by a magnetic flowmeter 35 when the stream is directed to the Analyzer(s) 39. In some embodiments, a source of deionized (DI) water is provided in the process from a set of ion-exchange cartridges 38. The pressurized DI water is allowed to flow to the Analyzer(s) when the electronic solenoid valve 37 is opened, which automatically results in closure of the 3-way sample valve 34. In this configuration the SSCC continues to process sample but the Analyzer(s) 39 measure the DI water stream to provide baseline "zero" data.

In some embodiments, the SSCC system comprises a fully-automated programable logic control (PLC) control system 41. The PLC system can be configured to run, control, monitor, transfer (e.g., to other local or remote computer systems) and/or record data from any component of the SSCC system. For example, in some embodiments, the PLC system is configured to run, control, monitor, transfer and/or record all SSCC process data, including the steam sample and condensate flowrates. In some embodiments, the PLC system controls the amount of steam condensation to a preset value by controlling the cooling water flow (control valve). In some embodiments, the PLC system controls the Separator level by controlling the condensate flow control valve to Analyzer(s). In still other embodiments, the PLC system calculates the steam sample concentration factor, X, where X=steam sample flow/condensate sample flow. In some embodiments, a SSCC system of the invention is utilized with a geothermal steam power-generating system and/or device. The invention is not limited to any particular steam-cycle power-generating system, steam generator or industrial process steam system. Exemplary systems include, but are not limited to, geothermal, coal-fired, oil-fired, biomass and nuclear power stations, industrial steam heating and cooling systems, steam sanitizing systems, and steam generators for enhanced oil recovery and other industrial applications.

In some embodiments, the SSCC system comprises a Steam Purity Analyzer(s) 39. The invention is not limited to any particular Analyzer. Indeed, there are a variety of commercially available Analyzers that find use in the invention. In fact, any commercial instruments designed for measuring impurities in condensed steam samples may be used. Exemplary Analyzers include, but are not limited to, one or more Analyzers manufactured by Hach, Loveland, Colo., USA (e.g., Hach Model 9245 low-level sodium Analyzer based on ion-specific electrode (ISE); Hach Model 5500sc low-level silica Analyzer based on color spectrophotometry; Hach Model EZ2005 low-level total iron Analyzer based on color spectrophotometry; and/or Hach Model TU5300 low-level turbidity (TSS) Analyzer based on laser light scattering).

I. Definitions

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the term "comprising" is intended to mean that the systems, devices, and methods include the recited elements, but not excluding others. Accordingly, it is intended that the systems, devices, and methods can include additional steps and features/elements (comprising).

The systems, devices, and methods of using the same of the present invention are further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

EXAMPLES

Example 1

Laboratory Test Results of SSCC

Calculations were performed to compare the conventional practice of full steam condensation with nitrogen (N2) gas purging for on-line analysis applications to that of a SSCC system and process with partial steam condensation of the present invention. Although not utilized in conventional methods, acid addition was also modeled in the full condensation process to assist in the removal of dissolved $CO_2$ and $H_2S$. The computer model used was developed specifically for the liquid/gas partitioning of $H_2S$, $CO_2$ and $NH_3$ in geothermal steam process applications (e.g., power plant condensers and gas removal). The program is called "One-Box", a subroutine of CNDSR, originally developed by Oleh Weres at Lawrence Berkeley Laboratories (1985, LBID-622).

Figure 3:
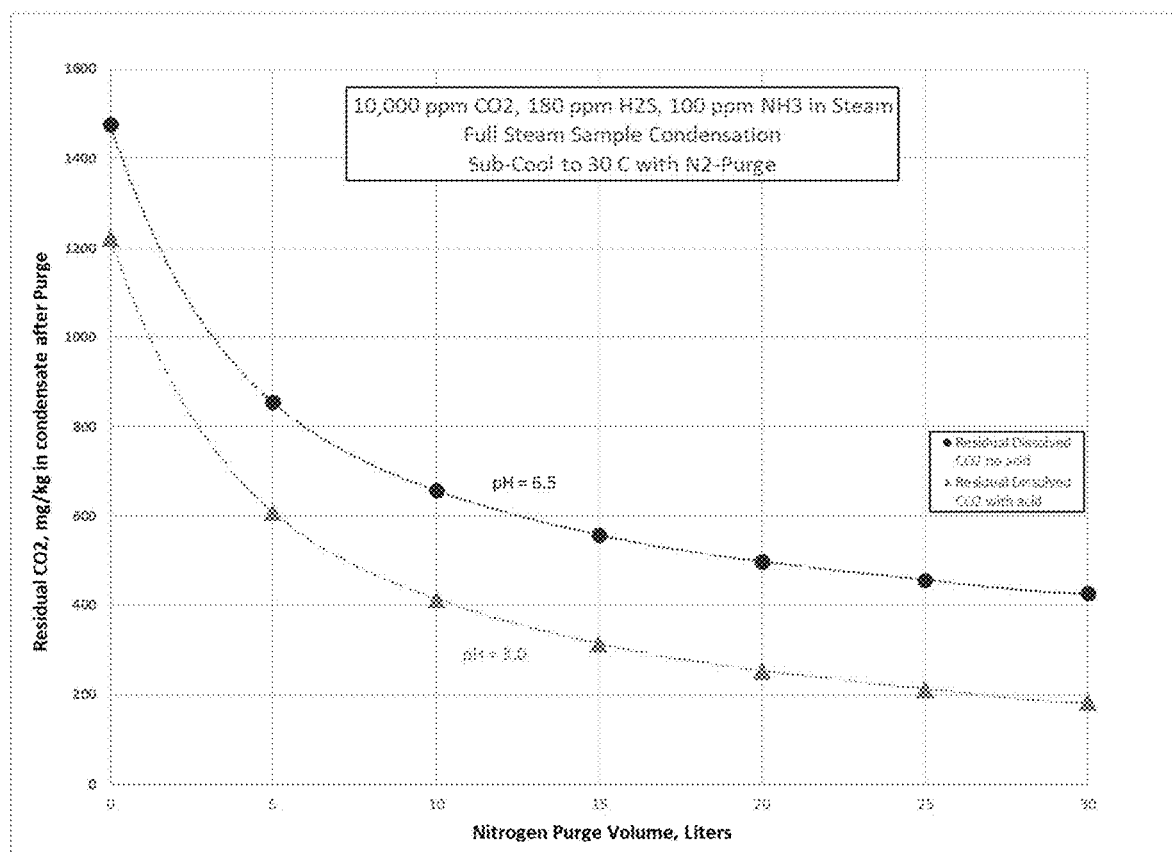
FIG. 3 shows calculated residual $CO_2$ dissolved in fully-condensed steam as a function of N2 purge gas volume to degas condensate with and without acid addition for pH adjustment.

FIG. 3 shows the residual dissolved $CO_2$ concentration in a fully-condensed steam sample as a function of the N2 purge-gas volume passed through the condensate, with and without acid added to reduce the pH from the natural state of 6.5 to 3.0. The original steam composition used for the computer model was 10,000 ppm CO2, 180 ppm H2S and 100 ppm NH3, which is approximately a median geothermal steam composition with respect to the noncondensable gases. As shown in FIG. 3, the dissolved CO2 concentration dropped rapidly with initial purging, but then leveled-out after about 30 liters of gas-purge volume, with no significant benefit after about 50 liters. A typical N2 purge-gas flowrate in an on-line Analyzer would be about 1 liter per minute (lpm), so volumes much more than 5 or 10 liters are not practical for an on-line Analyzer that needs to monitor impurities in steam nearly real-time (analysis should be <5 minutes per sample). At a 10-liter purge volume, there would be 6.5% of the total CO2 still dissolved in the condensate and 4.0% still dissolved given the same purge volume with the pH reduced to 3.0.

Figure 4:
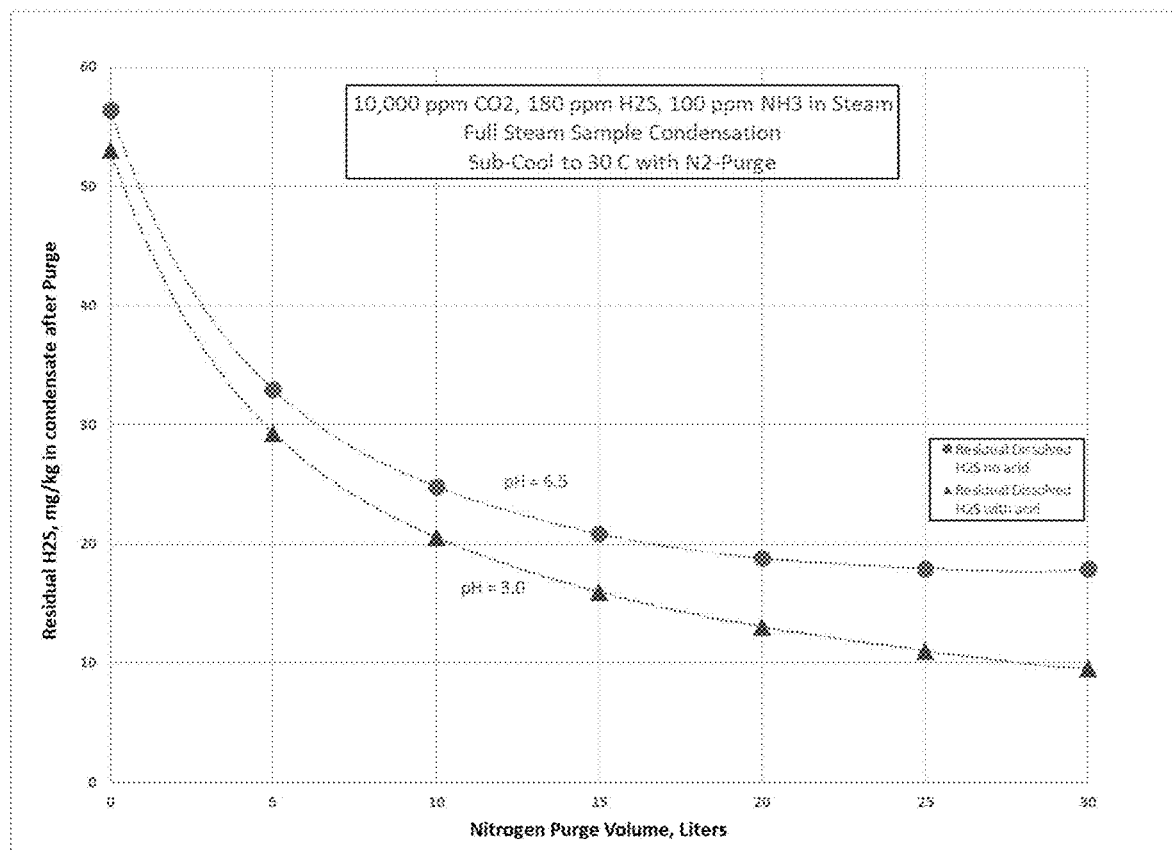
FIG. 4 shows calculated residual $H_2S$ dissolved in fully-condensed steam as a function of N2 purge gas volume to degas condensate with and without acid addition for pH adjustment.

FIG. 4 shows the residual dissolved H2S concentration in a fully-condensed steam sample as a function of the N2 purge-gas volume passed through the condensate, with and without acid added to reduce the pH from 6.5 to 3.0. The same steam composition was used as shown in FIG. 3. Upon full condensation with no gas purging, about 30% of the total H2S in the steam dissolved in the condensate. There is little benefit to acid addition with no gas purging. After a 10-liter purge volume, there is 14% of the total H2S still dissolved in the condensate and 11% still dissolved given the same purge volume with the pH reduced to 3.0. There is no significant benefit in reducing dissolved H2S after about 30 liters of gas purging, regardless of pH.

Figure 5:
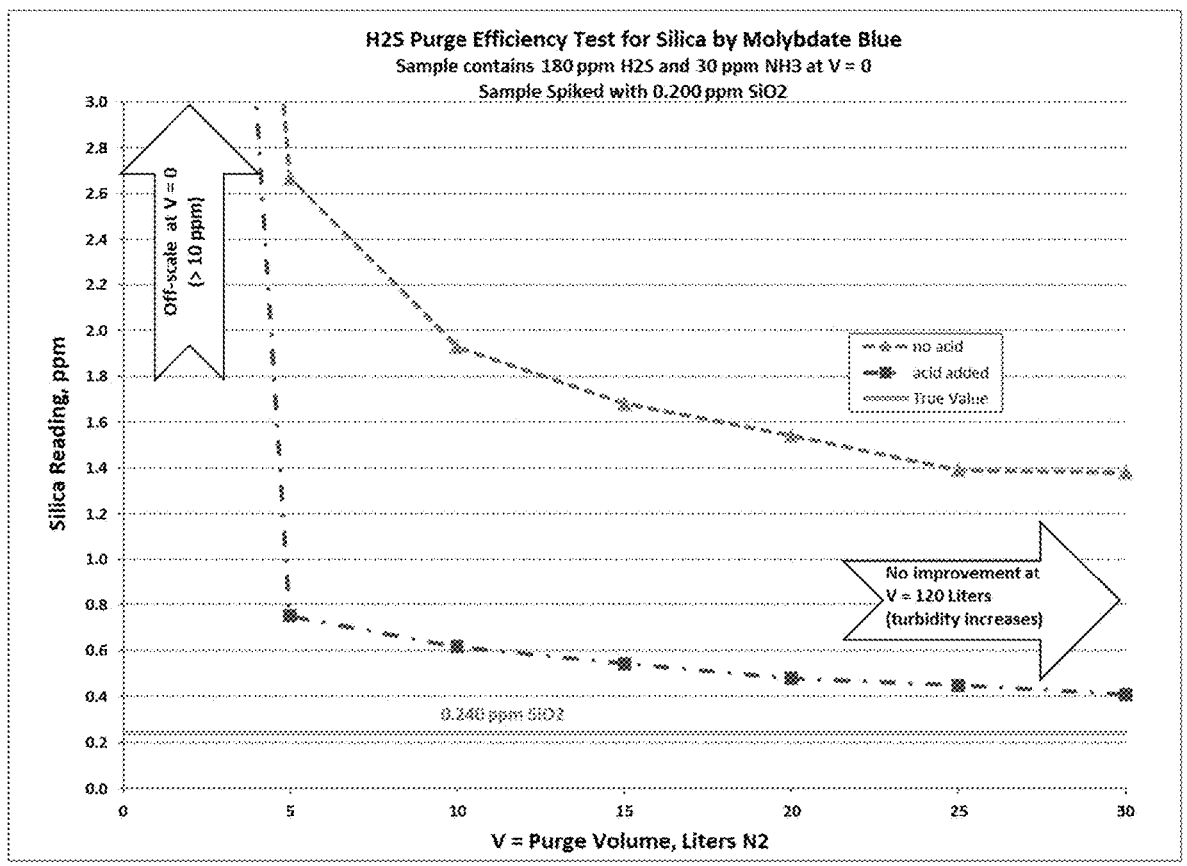
FIG. 5 shows the measured residual $H_2S$ dissolved in an actual steam condensate sample as a function of N2 purge gas volume to degas condensate with and without acid addition for pH adjustment.

Controlled laboratory tests were also performed to confirm the chemical modeling results on H2S gas-purging efficiency. FIG. 5 shows the measured residual $H_2S$ dissolved in an actual steam condensate sample as a function of N2 purge gas volume to degas condensate with and without acid addition for pH adjustment. In this case the steam condensate sample contained 180 ppm H2S and 30 ppm NH3. The measured silica content of the original sample was 0.040 ppm, and 0.200 ppm was added to make a known concentration of 0.240 ppm in order to make the detection of silica easier in the presences of the H2S interference. The concentration of silica measured by the Molybdate colorimetric method, the same used by all on-line Analyzers for low-level silica measurement in steam, is plotted versus the gas purge volume. As observed using the chemical modeling experiments and results for H2S described in FIGS. 4 and 5, measured silica value dropped quickly with the first 5 liters of gas purging, but again leveled-out at about 30 liters, with and without acid addition. The high silica values measured compared to the true value of 0.240 ppm was due to the H2S interference. Even after 120 liters of gas purge with acid added the measured value was almost double the true value due to the residual dissolved H2S interference and the formation of turbidity as this H2S slowly oxidizes in the sample.

Figure 6:
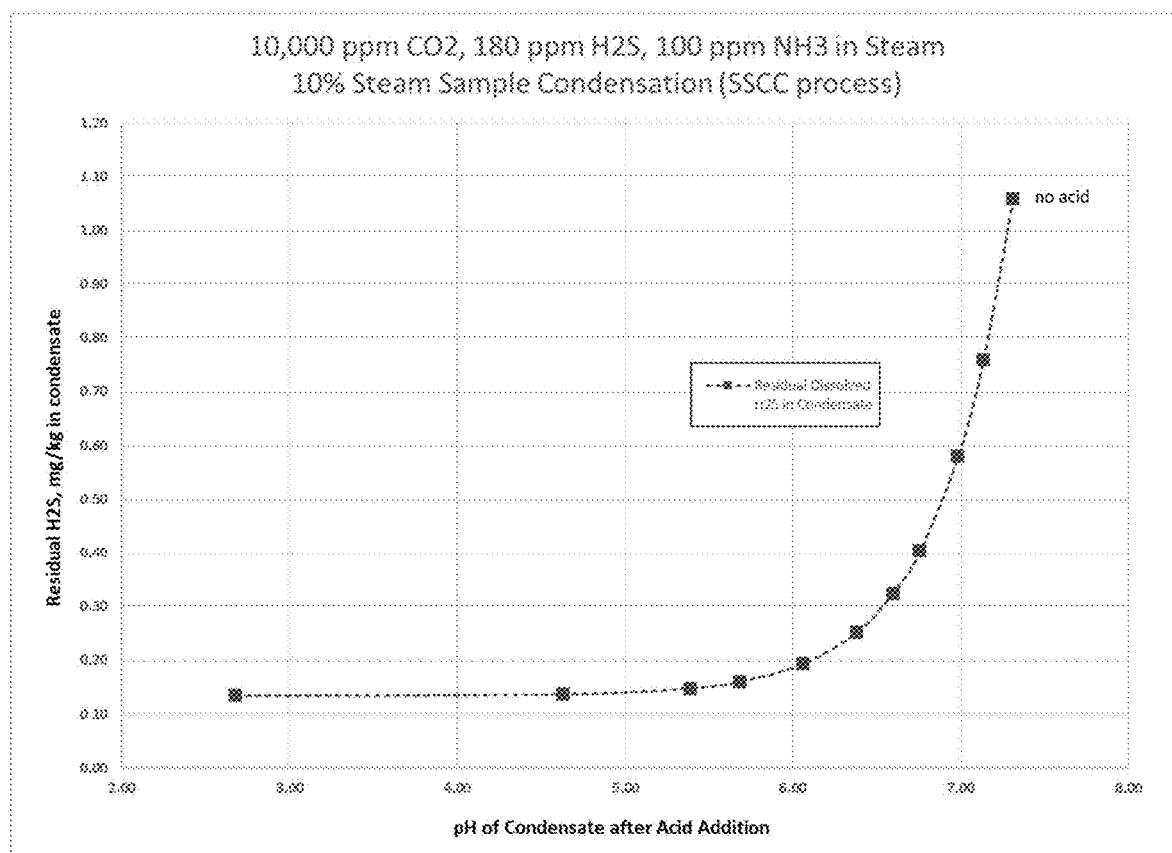
FIG. 6 shows the calculated results from a model of the SSCC process for residual $H_2S$ dissolved in partially-condensed steam at 100 C as a function of acid addition for pH adjustment, using the same model and steam composition as in FIGS. 3 and 4.

The SSCC system of the present invention provides on-line steam purity analysis that prevents interfering gases dissolution in the condensate in the first place. FIG. 6 shows the calculated results from a model of the SSCC process for residual H2S dissolved in partially-condensed steam at 100 C as a function of acid addition for pH adjustment, using the same model and steam composition described in FIGS. 3 and 4. With no acid added, only about 0.5% of the total H2S in the steam dissolved in the condensate. With acid addition to pH 5 or less, only 0.07% of the total H2S in the steam dissolved in the condensate. This is over 2 orders of magnitude less H2S dissolved in the condensate than can be achieved with the full-condensation process using N2 purging and acid addition.

Multiple prototypes of a SSCC systems described herein have been fabricated and tested. A fully-functional and automated SSCC depicted in the drawings and described herein was tested using a laboratory steam generator test loop to simulate power plant turbine steam. The SSCC was tested at full design flowrates (1 kg/h steam, 0.10 kg/h condensate) and inlet pressure of 6.5 bara with saturated and superheated steam temperatures up to 225 C.

The SSCC requires efficient separation of the condensate produced from the residual steam vented. The impurity concentration factor, X as described herein, uses the measured condensate flow after the steam/liquid separator (see, e.g., separator 9 as shown in FIG. 1) in the concentration factor calculation. Therefore, if the condensate flowrate measured is low due to liquid carry-over with the residual vented steam, the concentration factor X will be erroneously high. A test was performed on the SSCC using the steam test loop to determine the amount of liquid carry-over into the steam from the separator 9. A highly-detectable tracer (e.g., a fluorescent dye marker (e.g., PTSA)) only soluble in the liquid phase (no vapor partitioning), was injected into the steam flow upstream of the Contactor 6 by a precise metering pump. Samples of the condensate produced through normal operation of the SSCC (where the inlet steam flow was 1 kg/h and X=10), and samples of fully-condensed vent steam from the separator (using an auxiliary shell-and-tube heat exchanger) were both analyzed for the tracer content. The results listed in FIG. 7 shows that the amount of liquid carry-over with the steam from the separator was only about 0.2%. This was well below a level of measurement bias that would require a mathematical correction to the results. Typically, the measurement accuracy of each impurity by the commercial Analyzers is not better than +/−10%.

A test was also performed to directly measure the concentration factor and recovery efficiency of steam impurities through the SSCC process. A known concentration solution of NaCl (10.3 ppm) was injected upstream of the Contactor 6 by a precise metering pump. The injection rate was determined gravimetrically using an electronic balance to measure the weight loss of the solution from a reservoir over time. The average injection rate of the solution was 9.8 +/−0.1 g/min. The measured condensate flowrate produced by the SSCC during the test was 0.0994 g/min (0.100 lpm at 35 C). Under these conditions the expected concentration of Na in the condensate was 1.02 ppm and the average measured concentration by the on-line sodium Analyzer was 0.99 ppm, as shown in FIG. 8. Again, this was well below a level of measurement bias that would require a mathematical correction to the results given the accuracy of the on-line Analyzers. The actual Na concentration in the sample inlet steam was 0.10 ppm based on the steam flowrate of 1.0 kg/min and the known Na solution injection rate. Accordingly, in some embodiments, the invention provides a SSCC system that is highly efficient in trapping, concentrating and retaining non-volatile impurities in geothermal steam while effectively preventing the dissolution of interfering noncondensable gases into the sample stream.

It will be apparent to those skilled in the art that various modifications and variations can be made in the systems, devices, and methods of the present invention without departing from the spirit or scope of the invention. Thus, it is intended that the present invention cover the modifications and variations of this invention provided they come within the scope of the appended claims and their equivalents.

What is claimed:

1. A method for determining steam purity in a raw steam stream comprising use of a device comprising:
    a. one or more devices that maintain isokinetic flow of a steam sample through an isokinetic sample probe nozzle;
    b. a Desuperheat pump that prevents the steam sample stream from becoming superheated after the isokinetic flow control device;
    c. a steam contactor that condenses the steam sample stream;
    d. a steam/condensate separator that separates the condensate sample stream from the residual steam stream sample;
    e. a steam condensate sample flowmeter that measures the flowrate of the condensate sample stream; and
    f. one or more analyzers that measure impurities.

2. A method for determining steam purity in a raw steam stream comprising:
    obtaining a steam stream sample from the raw steam stream;
    partial condensation of the steam stream sample to generate a condensate sample stream;
    separating the condensate sample stream from the residual steam stream sample;
    analysis of the condensate sample stream comprising detecting and/or measuring one or more impurities in the condensate sample stream;
    measuring the steam stream sample flow rate and the condensate sample stream flow rate;
    calculating a concentration factor utilizing the measured steam stream sample flow rate and condensate sample stream flow rate;
    using the concentration factor to calculate the level of the one or more impurities in the raw steam stream.

3. The method of claim 2, wherein a vapor/liquid Separator is used for the separation of the condensate sample stream from the residual steam stream sample.

4. The method of claim 3, wherein the vapor/liquid Separator has a separation efficiency of greater than 99%.

5. The method of claim 2 wherein the one or more impurities are selected from the group consisting of sodium (Na), silica (SiO2), chloride (Cl), iron (Fe) and total suspended solids (TSS).

6. The method of claim 2, wherein partial condensation of the steam stream sample prevents the dissolution of noncondensable gases (NCG) from the steam stream sample into the condensate sample stream.

7. The method of claim 6, wherein prevention of the dissolution of noncondensable gases (NCG) from the steam stream sample into the condensate sample stream provides a more accurate measurement of the impurities in the steam stream sample than in the absence of partial condensation.

8. The method of claim 2, wherein using the concentration factor to calculate the level of the one or more impurities in the raw steam stream permits measurement of the one or more impurities at a detection level of 1 part per billion.

9. The method of claim 2, wherein the partial condensation of the steam stream sample removes bulk noncondensable gases from the steam stream sample.

10. The method of claim 2, wherein the method does not utilize air and/or nitrogen purging.

11. The method of claim 2, wherein the steam stream sample flow is controlled to maintain an isokinetic flow rate.

12. The method of claim 2, wherein the method does not utilize ion-exchange cartridges for preconcentration or pretreatment.

13. The method of claim 2, wherein partial condensation of the steam stream sample concentrates the steam stream sample by at least an order of magnitude.

14. The method of claim 2, wherein the raw steam stream is selected from the group consisting of steam used for power generation, geothermal steam, steam used for oil recovery, steam used for heating, steam used for cooling, steam used for food processing, and steam used for medical sterilization applications.

15. The method of claim 2, wherein a metering pump doses dilute acid into the sample steam stream after the desuperheater.

16. The method of claim 15, wherein the dilute acid is selected from the group consisting of HCl, $H_2SO_4$, and acetic or citric acid.

17. The method of claim 15, wherein the acid in the sample steam stream prevents the dissolution of $H_2S$ into the condensate to a level <1 ppm $H_2S$ in the presence of $NH_3$ in the steam sample present at >1 ppm $NH_3$.

18. The method of claim 2, wherein the steam sample is partially condensed under a precisely-controlled condensation process in a single-tube shell-and-tube heat exchanger.

19. A device for determining steam purity comprising:
    a. one or more devices that maintain isokinetic flow of a steam sample through an isokinetic sample probe nozzle;
    b. a Desuperheat pump that prevents the steam sample stream from becoming superheated after the isokinetic flow control device;
    c. a steam contactor that condenses the steam sample stream;
    d. a steam/condensate separator that separates the condensate sample stream from the residual steam stream sample;
    e. a steam condensate sample flowmeter that measures the flowrate of the condensate sample stream; and
    f. one or more analyzers that measure impurities.

20. The device of claim 19, wherein the one or more devices that maintain isokinetic flow is a flow sensor with a flow control valve.

21. The device of claim 19, wherein the one or more devices that maintain isokinetic flow is a critical orifice with an upstream pressure sensor.

22. The device of claim 19, wherein the Desuperheat pump prevents the deposition of impurities.

23. The device of claim 19, wherein the steam contactor partially condenses the steam sample stream.

24. The device of claim 23, wherein partial condensation occurs under a precisely-controlled condensation process with a static mixer to ensure contact and transfer of impurities from the steam sample stream to the condensate sample stream.

25. The device of claim 19, wherein the steam sample stream flowrate and the condensate sample stream flowrate are utilized to calculate a concentration factor, wherein the concentration factor equals the steam inlet sample flowrate/ condensate outlet sample flowrate.

26. The device of claim 25, wherein the concentration factor is used to correct the analyzed concentration back to the original concentration of impurity in the raw steam.

27. The device of claim 19, wherein the analyzer measures impurities selected from the group consisting of sodium (Na), silica (SiO2), chloride (Cl), iron (Fe) and total suspended solids (TSS).

\* \* \* \* \*